Figure 1:
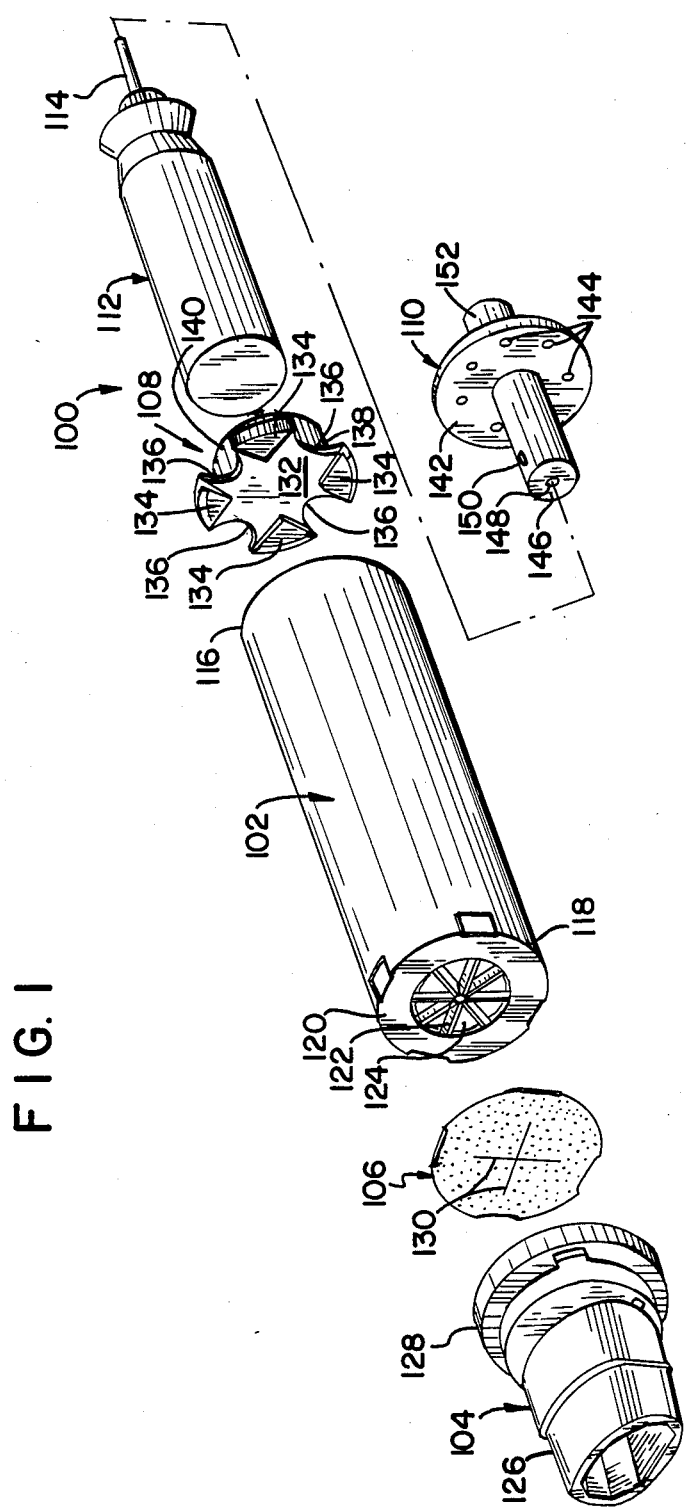

United States Patent [19]

Sperry

[11] Patent Number: 4,852,561
[45] Date of Patent: Aug. 1, 1989

[54] INHALATION DEVICE

[76] Inventor: Charles R. Sperry, 113 Clinton St., Springfield, Vt. 05156

[21] Appl. No.: 224,883

[22] Filed: Jul. 27, 1988

[51] Int. Cl.[4] .............................................. A61M 15/00
[52] U.S. Cl. ........................... 128/200.23; 128/203.15; 128/200.18
[58] Field of Search ....................... 128/200.23, 200.18, 128/203.15, 203.23, 203.13, 203.12

[56] References Cited

U.S. PATENT DOCUMENTS

| | | | |
|---|---|---|---|
| 3,560,070 | 2/1971 | Hanson et al. | 128/173 |
| 3,732,864 | 5/1973 | Thompson et al. | 128/173 R |
| 3,814,297 | 6/1974 | Warren | 222/402.13 |
| 3,826,413 | 7/1974 | Warren | 222/402.13 |
| 4,414,972 | 11/1983 | Young et al. | 128/200.23 |
| 4,470,412 | 9/1984 | Nowacki et al. | 128/200.18 |
| 4,484,577 | 11/1984 | Sackner et al. | 128/203.28 |
| 4,534,343 | 8/1985 | Nowacki et al. | 128/200.23 |
| 4,570,630 | 2/1986 | Elliott et al. | 128/203.15 |
| 4,952,348 | 6/1986 | Waters, IV et al. | 128/200.23 |

FOREIGN PATENT DOCUMENTS

| | | | |
|---|---|---|---|
| 699313 | 12/1964 | Canada | 128/200.18 |
| 8502778 | 7/1985 | World Int. Prop. O. | 128/203.15 |

*Primary Examiner*—Edgar S. Burr
*Assistant Examiner*—Kimberly L. Asher
*Attorney, Agent, or Firm*—Lerner, David, Littenberg, Krumholz & Mentlik

[57] ABSTRACT

An inhalation device in the nature of a metered dose inhaler is designed specifically for existing respiratory drugs to be employed in hospitals and/or by patients at home. The device is constructed of a housing which defines an aerosol chamber for a metered dose of a medicant containing aerosol from a cartridge. The cartridge is supported wholly within the aerosol chamber. An actuating valve mechanism is slidingly receiving within an open end of the housing and includes a projecting portion to which a compressive force may be applied. Upon application of the compressive force, for example, by forcing the open end of the housing against a supporting surface, the outlet valve mechanism of the cartridge is activated to dispense a metered dose of medicant into the aerosol chamber in the form of an aerosol.

26 Claims, 3 Drawing Sheets

INHALATION DEVICE

BACKGROUND OF THE INVENTION

The present invention relates in general to an inhalation device, and more particularly, to such a device for use with a cartridge having an outlet valve mechanism from which a medicant contained in the cartridge may be discharged in metered dosages in the form of an aerosol.

More than 21 million individuals in the United States suffer from asthma, chronic bronchitis or emphysema, and at least 5.25 million of them regularly use a metered dose inhaler (MDI). The use of MDIs is recognized as one of the most effective methods for the treatment of these and other respiratory problems. Physicians are considering the issues of compliance for typical MDIs and are prescribing enhancement devices for these MDIs or are specifying MDIs with features that improve drug inhalation technique and efficacy.

The majority of the medication dispersed from an MDI does not reach the lungs, but is deposited on the linings of the mouth and upper respiratory track. Seventy percent of the medication is typically lost by inelastic collision of the large mass and high velocity particles with the interior walls. Aerosols reaching the lungs have been known to have particles ranging in size from 2.5 to 5.5 um. With normal breathing, 50% of the medication reaching the lungs is often exhaled. When one's breath is held, time is allowed for the slower moving particles to impact the lung walls and to be retained, resulting in only about 10% of the medication being exhaled. The holding of one's breath is often impossible during, for example, an asthmatic attack.

MDI aerosols are inherently large momentum particles due both to their size and speed, as opposed to the optimum fine mist desired. The particles exiting from the pressurized medication containing cartridge have a size typically in the range of from 20 to 50 um. The large particle size is due to incomplete vaporization of the propellant, with the factors of temperature, concentration and time playing important rolls. Adiabatic expansion of the propellant cools the particles thereby competing against the formulation of the fine mist desired. The vapor is initially saturated thereby increasing the time for the particles to evaporate. The vaporization time can range from 0.3 msec for a dilute vapor to 0.8 sec for a saturated vapor. The propellant pressure is considered to play only a minor roll in particle size. For example, increasing the pressure from 45 to 80 PSI, decreases the particle size only from 3.7 to 2.2 um. Thus, known MDIs are generally inefficient and ineffective in converting the medication into a fine mist of particles that can be deposited in the proper bronchial area to relieve an asthmatic attack.

Devices that administer the proper amount of medication to specific locations of the lower respiratory system paired with drugs that are specially prepared and packaged to optimize the device are known, for example, from Hanson et al., U.S. Pat. No. 3,565,070, Thompson et al., U.S. Pat. No. 3,732,864, Warren, U.S. Pat. No. 3,814,297, Warren, U.S. Pat. No. 3,826,413, Young et al., U.S. Pat. No. 4,414,972 and Waters, IV et al., U.S. Pat. No. 4,592,348. Although these devices provide a convenient and effective MDI system, they must be used correctly in order to obtain an effective dosage. As the MDI aerosol is dispensed under pressure as a single shot, it is required that the user time each breath with the MDI aerosol discharge. The full dose of medication will frequently not be delivered deep within one's lungs if this timing is not synchronized. In addition, for those reasons previously discussed, only a small portion of the MDI aerosol is retained on the lung walls.

In order to increase the efficiency of these known MDIs, auxiliary devices have been designed to perform two pharmalogical functions, namely, reduction of medication deposited in the upper airways and increasing the medication deposited in the lungs. These auxiliary devices are known from Nowacki et al., U.S. Pat. No. 4,534,343, Sackner et al., U.S. Pat. No. 4,484,577 and Nowacki et al., U.S. Pat. No. 4,470,412, which provide a confined volume between the MDI and the users mouth. The large momentum particles are deposited in the auxiliary device instead of the upper airways of the user. It is the object of these auxiliary devices to improve drug delivery to the lungs by allowing the particles time to vaporize, in addition to providing more smaller particles having lower velocities. These for momentum particles can then follow the airflow through the upper airways and into the users lungs. There is still, however, the need for improvements in these MDIs and auxiliary devices to enhance their compactness, efficiency of operation and ease of use. In particular, there is the need to improve and simplify the mechanism for discharging the medication from the cartridge when the MDI is being used by children, elderly individuals and those with coordination problems.

SUMMARY OF THE INVENTION

The MDI of the present invention is designed to provide inexpensive, disposable, portable and effective drug delivery with the use of an all-in-one aerosol drug cartridge and integral aerosol chamber which employs a one-way valve to direct the users breath. The MDI is capable of administering agents which are stored in aerosol type cartridges employing fluorocarbon combinations of differing volatility and surfactants to achieve optimal aerosolization. The MDI can be tuned to each type of drug, propellant and cartridge type to assure effective drug delivery.

The MDI of the present invention employs aerosol chamber dispersion techniques to reduce such ailments as thrush and a one-way valve that allows the user to draw the drug from the aerosol chamber and exhale into the MDI without disturbing its contents or contaminating the MDI with exhaled organisms. This arrangement allows the user to take a number of relaxed breaths through the MDI and assures that the entire metered shot of medication has been inhaled without requiring coordinated action with breathing and activating the metered dose. The aerosol cartridge is located inside the aerosol chamber and is activated by a unique valve that directs the discharged contents into the aerosol chamber for aerosolization. The aerosol chamber is shaped to optimize the aerosolization process while maintaining a good shape to hold and carry about in a jacket pocket or purse.

The MDI of the present invention is an extremely easy device to operate with no required maintenance. The user simply shakes the device and activates the metered dose valve by pressing the device against a firm horizontal surface such as a table. The MDI's shape and optimally its center of gravity is configured in such a way as to make it obvious to the user which end to push against the table. By pushing the MDI against the table, the consideration of orientation for proper valve activation, and thus proper unit dosage, is assured. Because the MDI and the cartridge are an integral drug delivery device, a system of graphics to identify the drug, dose, warnings, lot numbers and date can be clearly printed on the aerosol chamber or a secured label.

One object of the present invention is to provide an MDI that meets the demands for better patient compliance by all user groups.

Another object of the present invention is to provide an MDI that is simple to use by children, elderly individuals and those with coordination problems.

In accordance with one embodiment of the present invention, there is disclosed an inhalation device for use with a cartridge having an outlet valve mechanism from which a medicant contained within the cartridge may be discharged in the form of an aerosol, the device is constructed of a hollow housing having a longitudinal axis, receiving means within the housing for receiving the cartridge therein, activating means moveable within one end of the housing and attached to the outlet valve mechanism for discharging a quantity of a medicant containing aerosol from the cartridge into that portion of the housing unoccupied by the cartridge, the activating means having a projecting member extending outwardly of the one end of the housing whereby depression of the member with a sufficient force discharging the medicant containing aerosol into the housing, and dispensing means at another end of the housing for dispensing the medicant containing aerosol from the housing to a user of the device.

In accordance with one embodiment of the present invention, there is disclosed an inhalation device for use with a cartridge having an outlet valve mechanism from which a medicant contained within the cartridge may be discharged in the form of an aerosol, the device is constructed of a hollow housing having a longitudinal axis, receiving means within the housing for receiving the cartridge therein, the interior of the housing unoccupied by the cartridge providing a chamber for the temporary storage of a quantity of medicant containing aerosol discharged from the cartridge, activating means at one end of the housing in operative association with the outlet valve mechanism for discharging the medicant containing aerosol into the chamber, and dispensing means at another end of the housing for dispensing the medicant containing aerosol from the chamber to a user of the device.

In accordance with one embodiment of the present invention, there is disclosed an inhalation device for use with a cartridge having an outlet valve mechanism from which a metered dose of a medicant contained within the cartridge may be discharged in the form of an aerosol to be inhaled by a user, the device is constructed of an elongated hollow housing having a longitudinal axis and a pair of opposed open ends, receiving means within the housing for releasably receiving the cartridge therein, the interior of the housing unoccupied by the cartridge providing an aerosol chamber for the temporary storage of the metered dose of a medicant containing aerosol discharged from the cartridge, activating means moveable within one open end of the housing and attached to the outlet valve mechanism for discharging the metered dose of the medicant containing aerosol from the cartridge into the aerosol chamber, the activating means having a first member attached to the outlet valve mechanism and received within the one open end of the housing and a second member projecting outwardly of the one open end of the housing, whereby depression of the second member with a sufficient force to effect longitudinal displacement of the first member within the housing causing the discharge of the medicant containing aerosol into the aerosol chamber, and dispensing means closing another open end of the housing for maintaining the metered dose of the medicant containing aerosol within the aerosol chamber while permitting the dispensing thereof from the housing to a user of the device by inhalation.

BRIEF DESCRIPTION OF THE DRAWINGS

The above description, as well as further objects, features and advantages of the present invention will be more fully understood with reference to the following detailed description of a presently preferred, but nonetheless illustrative, inhalation device, when taken in conjunction with the accompanying drawings, wherein:

FIG. 1 is an exploded unassembled view of the components of the inhalation device of the present invention;

FIG. 2 is a partial cross-sectional view of an assembled inhalation device in accordance with one embodiment of the present invention; and FIG. 3 is a partial cross-sectional view of an inhalation device in accordance with another embodiment of the present invention.

DETAILED DESCRIPTION

Referring now to the drawings, wherein like reference numerals represent like elements, there is shown in FIG. 1 an unassembled exploded view of the components of an inhalation device constructed in accordance with the present invention and generally designated by reference numeral 100. The inhalation device 100 is constructed of a housing 102, a breath tube assembly 104, a diaphragm valve 106, a cartridge receiving member 108 and an actuating valve mechanism 110. Also shown is a pressurized cartridge 112 containing the medicant to be discharged in the form of an aerosol. The cartridge 112 may contain a variety of medications suitable for treatment of asthma, chronic bronchitis, emphysema and the like. The cartridge 112 is of conventional construction so as to include outlet valve mechanism 114. The cartridge 112 is commercially available from any one of a number of pharmaceutical companies.

The housing 102 is cylindrical in shape having a circular open end 116 and an opposing partially open end 118. The partially open end 118 includes an annular flange 120 and a plurality of radial ribs 122 which define a plurality of triangular-shaped openings 124 therebetween.

The dispensing assembly 104 includes a breath tube 126 communicating with its hollow interior and an attachment member 128 for securing the dispensing assembly to the partially open end 118 of the housing 102. The dispensing assembly 104 is designed to allow the user to withdraw the medicant containing aerosol from within the housing 102 upon inhalation. To this end, a variety of known dispensing assemblies 104 may be employed with the present invention. For example, Nowacki et al., U.S. Pat. No. 4,470,412, discloses a one-way valve which opens upon inhalation without bypassing any ambient air into the inhaled mist, and which closes upon exhalation with the exhaled breath bypassed and not entered into the housing containing the medicant containing aerosol. As the dispensing assembly 104 forms no part of the present invention, a further discussion as to its construction will not be provided, rather, reference being made to the aforementioned Nowacki et al. patent.

The diaphragm valve 106 is constructed of a circular disk of elastomeric material having a pair of diagonal slits 130. The slits 130 are arranged at right angles to each other to provide enhanced flexibility of the diaphragm valve 106. However, it is to be understood that the diaphragm valve 106 may be constructed in other shapes and having an arrangement of slits 130 other than shown without departing from the present invention.

The cartridge receiving member 108 is constructed of a generally circular body 132 supporting on one face thereof four circumferentially spaced apart raised triangular-shaped members 134. The raised triangular-shaped members 134 are separated about the periphery of the circular body 132 by means of half-circular shaped openings 136. The opposing surface of the circular body 132 supports a circular member 138 provided with a central opening 140 sized to receive in sliding friction engagement the bottom end of the cartridge 112.

The actuating valve mechanism 110 is constructed of a generally circular plate 142 having a plurality of annularly arranged openings 144. One side of the plate 142 supports a circular rod 146 having an axial bore 148 communicating with a radial bore 150. The opposing surface of the circular plate 142 supports a second circular rod 152. The housing 102, dispensing assembly 104, cartridge receiving end 108 and actuating valve mechanism 110 may each be integrally molded from suitable plastic materials and the like.

The assembly of the thus far described components of the inhalation device 100 will now be described with reference to FIG. 2. The diaphragm valve 106 is positioned outwardly overlying and supported by the annular flange 120 and radial ribs 122 formed at the partially open end 118 of the housing 102. The diaphragm valve 106 is maintained in position upon securing the dispensing assembly 104 to the partially open end 118 of the housing 102 by means of its attachment member 128. The cartridge 112 is releasably secured to the cartridge receiving member 108 by pressing the base of the cartridge into sliding frictional engagement within the opening 140 of the circular member 138. The outlet valve mechanism 114 of the cartridge 112 is received in sliding frictional engagement within the axial bore 148 of the actuating valve mechanism 110. The thus far assembled cartridge receiving member 108, actuating valve mechanism 110 and cartridge 112 forms a subassembly which is inserted into the hollow of the housing 102.

The raised triangular-shaped members 134 of the cartridge receiving member 108 are positioned abutting the inside surface of the annular flange 120 such that the interior of the housing 102 communicates with the interior of the dispensing assembly 104 by an air passageway. The air passageway is formed by the half-circular shaped openings 136, the recessed area between the raised triangular-shaped members 134 and the circular body 132, and the triangular-shaped openings 124 provided between the radial rib 122 at the partially open end 118 of the housing 102. The actuating valve mechanism 110 is received within the housing 102 adjacent the circular open end 116. The peripheral edge of the circular plate 142 is in sliding arrangement with the interior surface of the housing 102. The rod 152 is dimensioned in its axial length so as to project outwardly beyond the extent of the housing 102 at the circular open end 116. The interior of the housing 102 not occupied by cartridge 112 provides an aerosol chamber 154 for receiving the medicant containing aerosol discharged from the cartridge.

The operation of the inhalation device 100 will now be described with reference to FIG. 2. The inhalation device 100 is gripped by the users hand about a portion of the housing 102. The inhalation device 100 is generally arranged in a vertical orientation with the rod 152 projection downwardly and the breath tube 126 projecting upwardly. The inhalation device 100 is positioned overlying a supporting surface, such as a table and the like, and forced downwardly against rod 152 with a sufficient force to effect longitudinal movement of the actuating valve mechanism 110 within the circular open end 116 of the housing 102 as indicated by the double-headed arrow 156. As the actuating valve mechanism 110 is displaced axially within the housing 102, the outlet valve mechanism 114 of the cartridge 112 is likewise displaced so as to discharge a metered quantity of medicant from the cartridge in the form of a medicant containing aerosol. The medicant containing aerosol is discharged through the axial bore 148 and radial bore 150 of the rod 146 and into the chamber 154. It is to be understood that the radial bore 150 may be arranged at an angle to axial bore 148 so as to extend, if preferred, rearwardly towards the cartridge receiving member 108.

With the aerosol chamber 154 filled with a metered dose of medicant containing aerosol, the user places the breath tube 126 in his mouth with the housing 102 arranged in a generally horizontal orientation. Upon inhalation, the medicant containing aerosol is withdrawn from the aerosol chamber 154 through the diaphragm valve 106 upon deflection of those material portions which allow the slits 130 to open. The openings 144 within the actuating valve mechanism 110 permit the ingress of air to prevent the formation of a partial vacuum within the aerosol chamber 154. Upon exhalation, the diaphragm valve 106 returns to its initial flat position with the slits 130 closed to prevent the exhaled breath from entering the aerosol chamber 154. Rather, the exhaled breath is bypassed to the surrounding atmosphere via the construction of the dispensing assembly 104. Further inhalation by the patient will continue to withdraw the medicant containing aerosol from the aerosol chamber 154. Thus, it is only required that the user inhale and exhale normally to obtain an effective treatment by the inhalation device 100 of the present invention. It can therefore be appreciated that the inhalation device offers significant advantages for users who have difficulty manipulating currently available metered dose inhalers due to lack of manual dexterity, age and the like.

Figure 3:
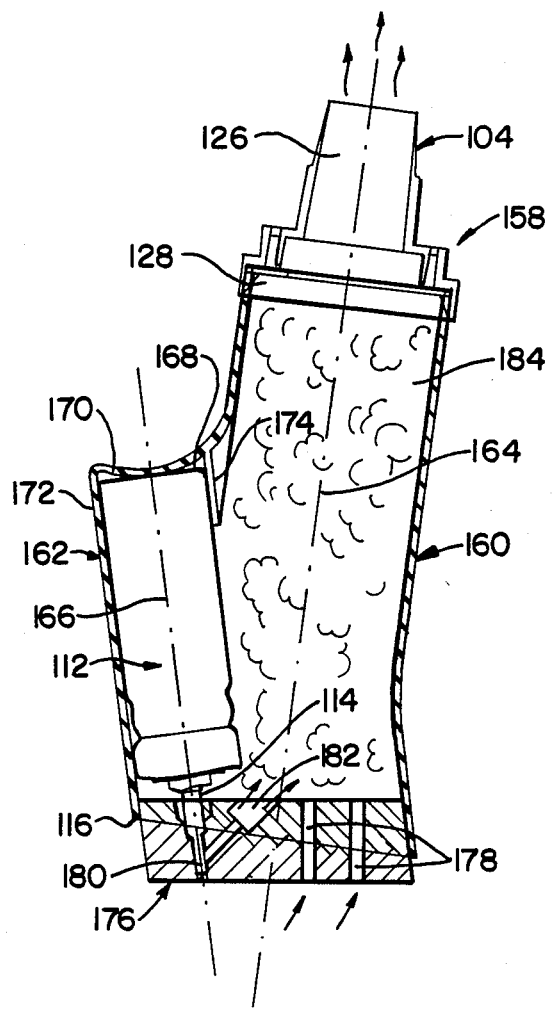

Turning now to FIG. 3, there is disclosed an inhalation device 158 constructed in accordance with another embodiment of the present invention. The inhalation device 158 includes a primary housing 160 having a lateral extension 162. The longitudinal axis 164 of the primary housing 160 is arranged at an angle to the longitudinal axis 166 of the lateral extension 162. The cartridge 112 is positioned inverted within the lateral extension 162 such that its base is slidingly received within an opening 168 formed by wall portions 170, 172 forming the lateral extension 162 and an inwardly projecting wall member 174. An actuating valve mechanism 176 is slidingly received within circular open end 116 of the housing 160 and lateral extension 162. The actuating valve mechanism 176 includes a plurality of openings 178, an axial bore 180 for receiving the outlet valve mechanism 114 of the cartridge 112, and an enlarged rearwardly facing bore 182 communicating between axial bore 180 and the interior of the housing 160 defined by aerosol chamber 184.

Figure 2:
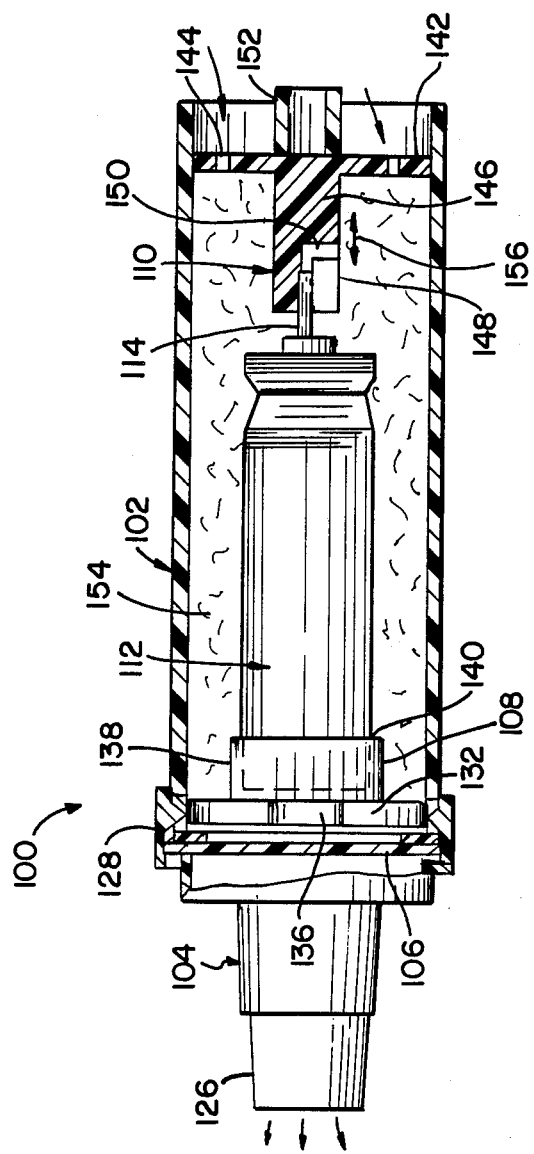

The operation of the inhalation device 158 is as previously described with respect to the inhalation device 100 illustrated in FIGS. 1 and 2. Briefly, depressing the actuating valve mechanism 176 with sufficient force against a supporting surface will cause dispensing of a metered dose of medicant from the cartridge 112 into the chamber 184. Although the inhalation device 158 is disclosed having a single cartridge 112, it is contemplated that the housing 160 may be provided with a plurality of lateral extensions 162 for receiving a corresponding plurality of cartridges 112. In this regard, the inhalation device 158 will provide a plurality of simultaneously metered dosages of medicant containing aerosols for inhalation by the user. A multiple cartridge containing inhalation device is an efficient way for the user to obtain application of an effective dosage of a plurality of different medicants simultaneously in a single application.

While the invention has been described in its preferred embodiments, it is to be understood that the words which have been used are words of description rather than limitation, and changes within the preview of the appended claims may be made without departing from the true scope and spirit of the invention in its broader aspects.

What is claimed is:

1. An inhalation device for use with a cartridge having an outlet valve mechanism from which a medicant contained within said cartridge may be discharged in the form of an aerosol, said device comprising a hollow housing having a longitudinal axis, and two ends located along said longitudinal axis receiving means within said housing for receiving said cartridge at least partially therein, activating means moveable within one of said ends of said housing and attached to said outlet valve mechanism for discharging a quantity of a medicant containing aerosol from said cartridge into that portion of said housing unoccupied by said cartridge, said activating means having a projecting member extending outwardly of said one end of said housing whereby depression of said member with a sufficient force causing discharging said medicant containing aerosol into said housing, and dispensing means at the other of said ends of said housing for dispensing said medicant containing aerosol from said housing to a user of said device.

2. The device of claim 1, wherein said housing is of cylindrical shape.

3. The device of claim 1, wherein said receiving means includes a body having a first portion adapted for engaging one end of said cartridge and a second portion adapted to permit dispensing of said medicant containing aerosol through said another end of said housing by providing a passageway therebetween.

4. The device of claim 1, wherein said activating means includes a body having a first portion adapted for attaching to said outlet valve mechanism, a second portion opposing said first portion forming said projecting member and a third portion intermediate said first portion and said second portion, said third portion slidingly engaging the inner surface of said housing to permit movement of said activating means therein.

5. The device of claim 4, wherein said third portion includes at least one opening providing communication between the interior of said housing and the surrounding atmosphere.

6. The device of claim 1, wherein said cartridge is arranged within said housing along said longitudinal axis.

7. The device of claim 1, wherein said cartridge is arranged within said housing at an angle to said longitudinal axis along a secondary longitudinal axis.

8. The device of claim 7, wherein said housing includes a lateral extension receiving said cartridge, said lateral extension arranged along said secondary longitudinal axis.

9. The device of claim 7, wherein said activating means is movable within said housing along said secondary longitudinal axis.

10. The device of claim 1, wherein said receiving means, said activating means and said cartridge, when assembled, form a unitary subassembly receivable within said housing.

11. An inhalation device for use with a cartridge having an outlet valve mechanism from which a medicant contained within said cartridge may be discharged in the form of an aerosol, said device comprising a hollow and two ends located along said longitudinal axis housing having a longitudinal axis, receiving means within said housing for receiving said cartridge at least partially therein, the interior of said housing unoccupied by said cartridge providing a chamber for the temporary storage of a quantity of medicant containing aerosol discharge from said cartridge, activating means at one of said ends of said housing in operative association with said outlet valve mechanism for discharging said medicant containing aerosol into said chamber, and dispensing mean at the other of said ends of said housing for dispensing said medicant containing aerosol from said chamber to a user of said device.

12. The device of claim 11, wherein said housing is of cylindrical shape.

13. The device of claim 11, wherein said receiving means includes a body having a first portion for engaging one end of said cartridge and a second portion adapted to permit dispensing of said medicant containing aerosol through said another end of said housing by providing a passageway therebetween.

14. The device of claim 11, wherein said cartridge is arranged within said housing along said longitudinal axis.

15. The device of claim 11, wherein said cartridge is arranged within said housing at an angle to said longitudinal axis along a secondary longitudinal axis.

16. The device of claim 15, wherein said activating means is movable within said housing along said secondary longitudinal axis.

17. The device of claim 11, wherein said activating means includes a projecting member extending outwardly of said one end of said housing for discharging the contents of said cartridge upon application of a sufficient force thereto.

18. An inhalation device for use with a cartridge having an outlet valve mechanism from which a metered dose of a medicant contained within said cartridge may be discharged in the form of an aerosol to be inhaled by a user, said device comprising an elongated hollow housing having a longitudinal axis and a pair of opposed open ends located along said longitudinal axis, receiving means within said housing for releasably receiving said cartridge therein, the interior of said housing unoccupied by said cartridge providing an aerosol chamber for the temporary storage of said metered dose of a medicant containing aerosol discharge from said cartridge, activating means moveable within one of said open ends of said housing and attached to said outlet valve mechanism for discharging said metered dose of said medicant containing aerosol from said cartridge into said aerosol chamber, said activating means having a first member attached to said outlet valve mechanism and received within said one open end of said housing and a second member projecting outwardly of said one open end of said housing, whereby depression of said second member with a sufficient force to effect longitudinal displacement of said first member within said housing causing the discharge of said medicant containing aerosol into said aerosol chamber, and dispensing means closing the other of said open ends of said housing for maintaining said metered dose of said medicant containing aerosol within said aerosol chamber while permitting the dispensing thereof from said housing to a user of said device by inhalation.

19. The device of claim 18, wherein said receiving means includes a body having a first portion adapted for releasably engaging one end of said cartridge and a second portion adapted to permit dispensing of said medicant containing aerosol through said another end of said housing by providing a passageway therebetween.

20. The device of claim 19, wherein said activating means includes a third member intermediate said first member and said second member, said third member slidingly engaging the inner surface of said housing to permit movement of said activating means therein.

21. The device of claim 20, wherein said third member includes at least one opening providing communication between the interior of said housing and the surrounding atmosphere.

22. The device of claim 18, wherein said cartridge is arranged within said housing along said longitudinal axis.

23. The device of claim 18, wherein said cartridge is arranged within said housing at an angle to said longitudinal axis along a secondary longitudinal axis.

24. The device of claim 23, wherein said housing includes a lateral extension receiving said cartridge, said lateral extension arranged along said secondary longitudinal axis.

25. The device of claim 23, wherein said activating means is movable within said housing along said secondary longitudinal axis.

26. The device of claim 18, wherein said receiving means, said activating means and said cartridge, when assembled, forming a unitary subassembly receivable within said housing.

* * * * *

UNITED STATES PATENT AND TRADEMARK OFFICE
CERTIFICATE OF CORRECTION

PATENT NO. : 4,852,561

DATED : August 1, 1989

INVENTOR(S) : Charles R. Sperry

It is certified that error appears in the above-identified patent and that said Letters Patent is hereby corrected as shown below:

Column 2, line 20, delete "for" and insert --low--.
Column 7, line 52, between "discharging said", insert --of--.
Column 8, line 30, after "low" insert --housing having a longitudinal axis--.
Column 8, line 40, "mean" should read --means--.

Signed and Sealed this

Nineteenth Day of June, 1990

Attest:

HARRY F. MANBECK, JR.

*Attesting Officer*      *Commissioner of Patents and Trademarks*